(12) United States Patent
Alpern

(10) Patent No.: US 6,644,469 B2
(45) Date of Patent: Nov. 11, 2003

(54) LARGE NEEDLE OVAL WOUND PLASTIC SUTURE PACKAGE

(75) Inventor: Marvin Alpern, Glen Ridge, NJ (US)

(73) Assignee: Ethicon, Inc., Somerville, NJ (US)

( * ) Notice: Subject to any disclaimer, the term of this patent is extended or adjusted under 35 U.S.C. 154(b) by 20 days.

(21) Appl. No.: 09/902,848

(22) Filed: Jul. 11, 2001

(65) Prior Publication Data
US 2003/0010655 A1 Jan. 16, 2003

(51) Int. Cl.[7] ............................................... A61B 17/06
(52) U.S. Cl. ................................... 206/63.3; 206/380
(58) Field of Search ............................... 206/63.3, 380, 206/227, 63.5, 382, 388

(56) References Cited

U.S. PATENT DOCUMENTS

| 4,884,681 A | 12/1989 | Roshdy et al. |
|---|---|---|
| 4,887,710 A | 12/1989 | Roshdy et al. |
| 4,946,043 A | 8/1990 | Roshdy et al. |
| 4,961,498 A | 10/1990 | Kalinski et al. |
| 4,967,902 A | 11/1990 | Sobel et al. |
| 5,052,551 A | 10/1991 | Cerwin et al. |
| 5,056,658 A | 10/1991 | Sobel et al. |
| 5,099,994 A | 3/1992 | Kalinski et al. |
| 5,131,533 A | 7/1992 | Alpern |
| 5,165,217 A | 11/1992 | Sobel et al. |
| 5,179,818 A | 1/1993 | Kalinski et al. |
| 5,180,053 A | 1/1993 | Cascio et al. |
| 5,230,424 A | 7/1993 | Alpern et al. |
| 5,236,083 A | 8/1993 | Sobel et al. |
| 5,249,671 A | * 10/1993 | Sinn ........................ 206/63.3 |
| 5,284,240 A | 2/1994 | Alpern et al. |
| 5,575,382 A | * 11/1996 | Sobel et al. ............... 206/63.3 |
| 5,665,652 A | 9/1997 | Shimizu |
| 5,894,921 A | * 4/1999 | Le et al. ................... 206/63.3 |
| 6,135,272 A | 10/2000 | Sobel et al. |

FOREIGN PATENT DOCUMENTS

| EP | 0575193 | 12/1993 |
|---|---|---|
| EP | 0728445 | 8/1996 |
| WO | 9741780 | 11/1997 |

* cited by examiner

Primary Examiner—David T. Fidei

(57) ABSTRACT

A tray package is provided for sutures and needles. The tray package includes a base member which has top and bottom surfaces. A needle park bridge is formed on the top surface and is sized and shaped to receive a needle of a suture. A suture channel is formed on the bottom surface and is sized and shaped to receive a suture.

12 Claims, 6 Drawing Sheets

LARGE NEEDLE OVAL WOUND PLASTIC SUTURE PACKAGE

FIELD OF THE INVENTION

The present invention relates to packages for armed sutures and more specifically to armed suture packages wherein the sutures are secured in a tray package.

BACKGROUND OF THE INVENTION

Armed sutures, i.e., sutures with a needle attached thereto, are typically packaged in packages that contain one or more sutures, which protect the sutures and needles during handling, shipping, and storage. The packages also facilitate access to and release of the sutures and needles for surgery. The packages may also be used for unarmed surgical sutures without needles.

Conventionally, two types of packages are used for surgical sutures and needles. The first type of package is a paper folder wherein a medical grade paperboard is cut and folded into a plurality of panels. The suture is manually wound onto a panel of the package. The remaining panels are then manually folded into an envelope configuration capturing the suture therein. The panels are then locked in place using slits and locking tabs that have been cut into the panels. Paper folder packages may be used to contain large size needles. The needles are typically separated from the suture strands by a paper panel so as to prevent the sharp points of the needles from damaging the suture.

The second type of package is a molded plastic tray package having a winding channel (hereinafter referred to as a suture channel). Tray packages typically have an oval shape with spaced outer and inner walls that form an oval suture channel. Unlike the paper folder package described above wherein the sutures are often manually wound, tray packages are mounted onto a winding fixture and then the sutures are automatically wound into the suture channel.

Tray packages conventionally employ what is known as a needle park that is configured to secure a surgical needle. Conventional needle parks may consist of foam members or equivalent retention structures, which are typically located on the same side of the tray package as the suture channel. Specifically, needles are parked in the "in-field" portion of the package, i.e., the portion of the package that is surrounded by the suture channel.

Although the two types of suture packages described above are adequate and effective for their intended use, there are disadvantages associated therewith. For example, the size and number of needles that may be packaged in conventional tray packages are limited by the "in-field" area. The alternative of using a much larger-sized tray package that may contain multiple sutures and larger needles also has drawbacks. Namely, larger-sized tray packages are not suitable to package single sutures or small-sized needles because of size and cost. Accordingly, multiple package sizes are required, which adds to manufacturing, stocking, and handling costs.

The use of paper folders also has disadvantages. Although paper folders may contain large and/or multiple needles, the sutures are typically manually wound, with correspondingly high manufacturing costs.

Accordingly, there is a need for suture packages that can contain a greater range of needle sizes and suture counts, that are readily adaptable to high-speed packaging processes, and that otherwise overcome the disadvantages of the prior art packages described above.

SUMMARY OF THE INVENTION

In accordance with the present invention, a suture package is disclosed which includes a base member having a top surface and a bottom surface opposite the top surface. First holding means is located on one of the surfaces and is provided for releaseably holding a needle. In addition, a second holding means is located on the other surface and is provided for holding a suture.

Other features and aspects of the present invention will become more fully apparent from the following detailed description of various exemplary embodiments, the appended claims and the accompanying drawings.

BRIEF DESCRIPTION OF THE DRAWINGS

For a more complete understanding of the present invention, reference is made to the following detailed description of various exemplary embodiments considered in conjunction with the accompanying drawings, in which.

DETAILED DESCRIPTION OF THE EXEMPLARY EMBODIMENTS

Figure 3:
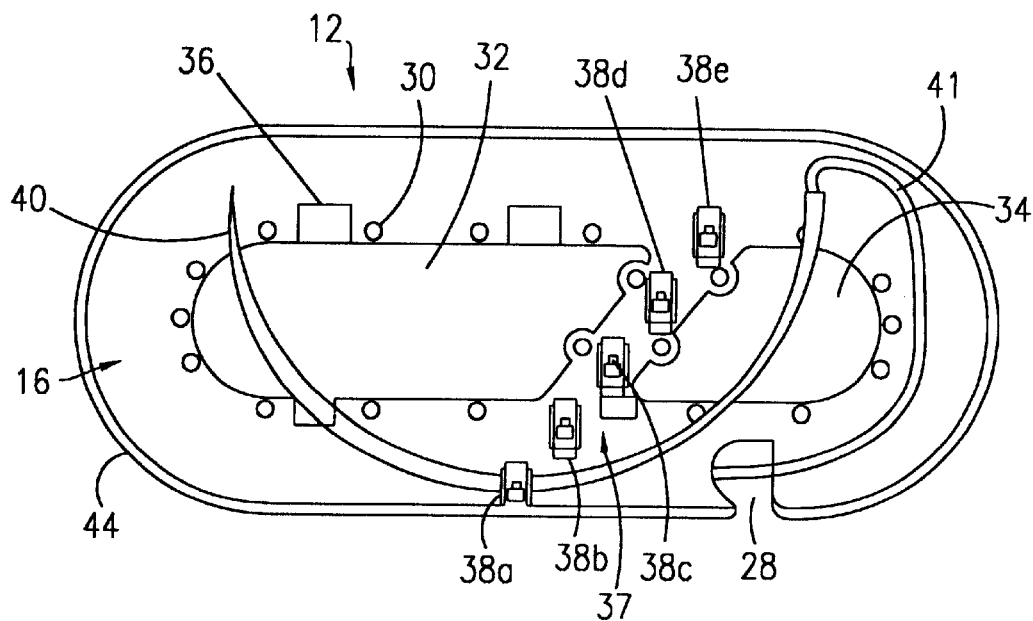
FIG. 3 is a top view of the base member of FIG. 1, with a needle shown in a parked position therein.

A tray package 10 (see FIG. 7) includes a base member 12 having a bottom surface 14 (see FIG. 1) and a top surface 16 (see FIG. 3). The base member 12 shown has a substantially oval shape, but it is understood that the base member 12 can have other shapes such as circular, square, and polygonal, etc.

Figure 1:
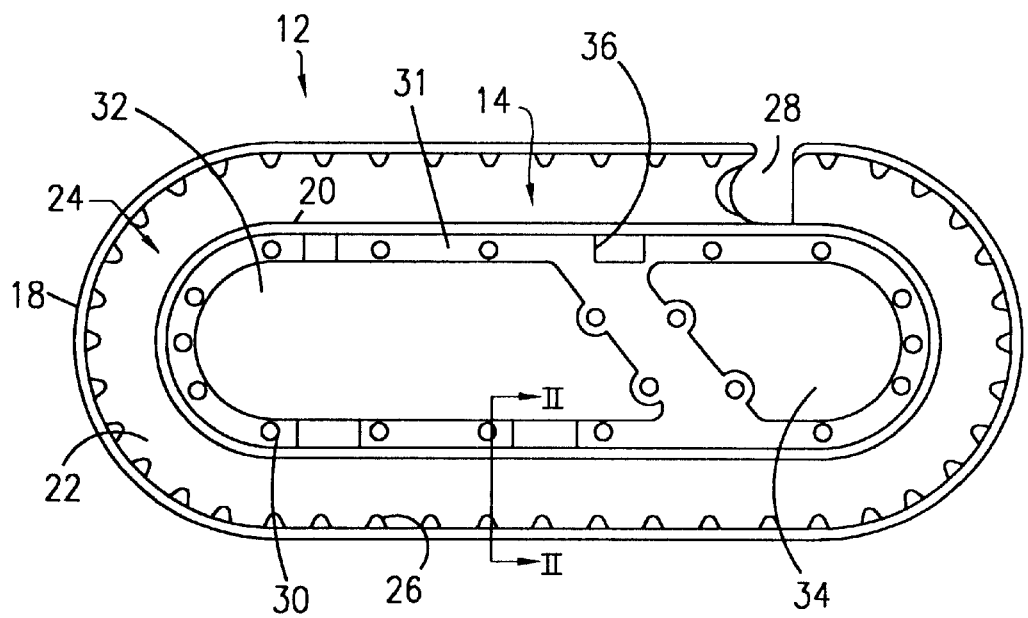
FIG. 1 is a bottom view of a base member of a suture package constructed in accordance with an exemplary embodiment of the present invention.

Referring to FIG. 1, the base member 12 has a downwardly extending outer peripheral wall 18 and a downwardly extending inner peripheral wall 20. The outer wall 18, the inner wall 20, and a portion 22 of the top surface 14 intermediate the outer wall 18 and the inner wall 20 form a suture channel 24 sized and shaped to releaseably hold and receive a suture.

Figure 2:
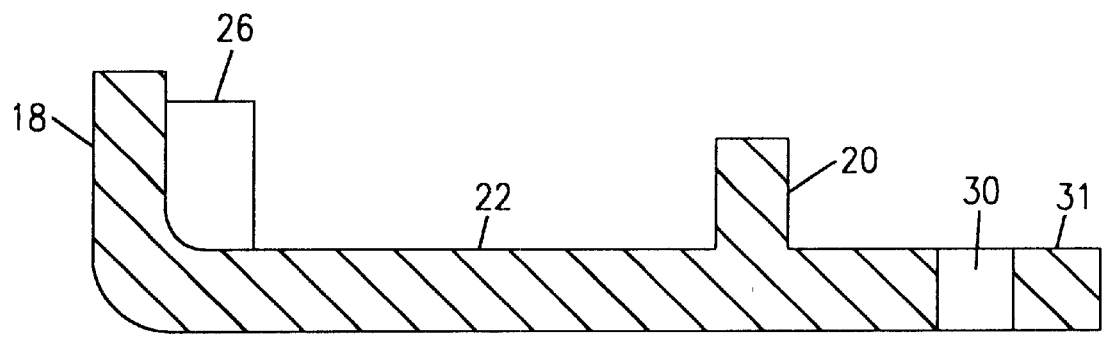
FIG. 2 is a cross-sectional view of the base member of FIG. 1, taken along line II—II and looking in the direction of the arrows.

The base member 12 further includes standoff members 26 which are integral with the outer wall 18 and which extend inwardly from the inner side of the outer wall 18. The standoff members 26 can be sized and shaped as described in U.S. Pat. No. 6,135,272, issued Oct. 24, 2000, the entire disclosure of which is incorporated herein by this reference. FIG. 2 shows the relative position of the outer wall 18, the inner wall 20, the intermediate portion 22, and the standoff members 26.

The base member 12 also has a passageway 28 (e.g., an opening) which is sized and shaped to allow a suture to traverse between the bottom surface 14 (FIG. 1) and the top surface 16 (FIG. 3). The passageway 28 is shown located between the outer wall 18 and the inner wall 20, although the passageway 28 may be formed along other areas on the base member 12.

The base member 12 further includes a plurality of rivet retention holes 30 which extend therethrough and which are positioned in a skirt 31 extending inwardly from the inner wall 20. The inner portion of the base member 12 has two large openings 32, 34. A plurality of cover cleat retention holes 36 are also employed, which are sized and shaped to retain an optional cover. A more detailed description of the foregoing features is described in U.S. Pat. No. 6,135,272, which has already been incorporated herein by reference.

With reference to FIG. 3, the top surface 16 of the base member 12 has a needle park bridge 37, which separates the two openings 32, 34 and which supports a plurality of needle parks 38a, 38b, 38c, 38d, 38e, each sized and shaped to receive and hold a needle 40 of an armed suture 41. Unlike a conventional tray package, which employs needle parks on the same side of the base member as the suture channel, the needle parks 38a–38e of the present invention are on the opposing side (i.e., the top surface 16) of the base member 12 relative to the suture channel 24, which is formed on the bottom surface 14 of the base member 12. Each needle park 38a–38e is designed to accommodate at least one needle. The needle 40 shown is of a large size relative to the size of the tray package 10. As can be appreciated, a plurality of needles of various sizes can be accommodated in the needle parks 38a–38e.

Figure 4:
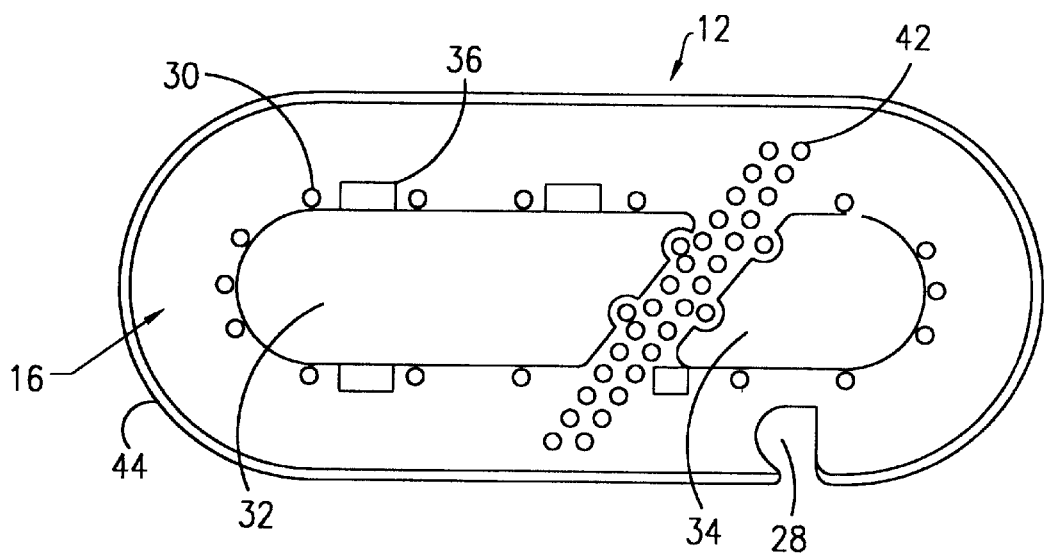
FIG. 4 is a top view of another exemplary embodiment of a base member constructed in accordance with the present invention.

Various designs for the needle parks 38a–38e may be used. For example, as shown in FIG. 4, a plurality of resilient, bristle-like pins 42, which project upwardly from the top surface 16 of the base member 12, function as a multi-position needle park. A cover (similar to the one designated by reference numeral 80 in FIG. 8) is used to hold the needle 40 which is supported by the pins 42.

The top surface 16 of the base member 12 also includes an upwardly extending outer wall 44 which surrounds the needle 40. The outer wall 44 is a continuous wall which extends around the perimeter of the top surface 16.

Figure 5:
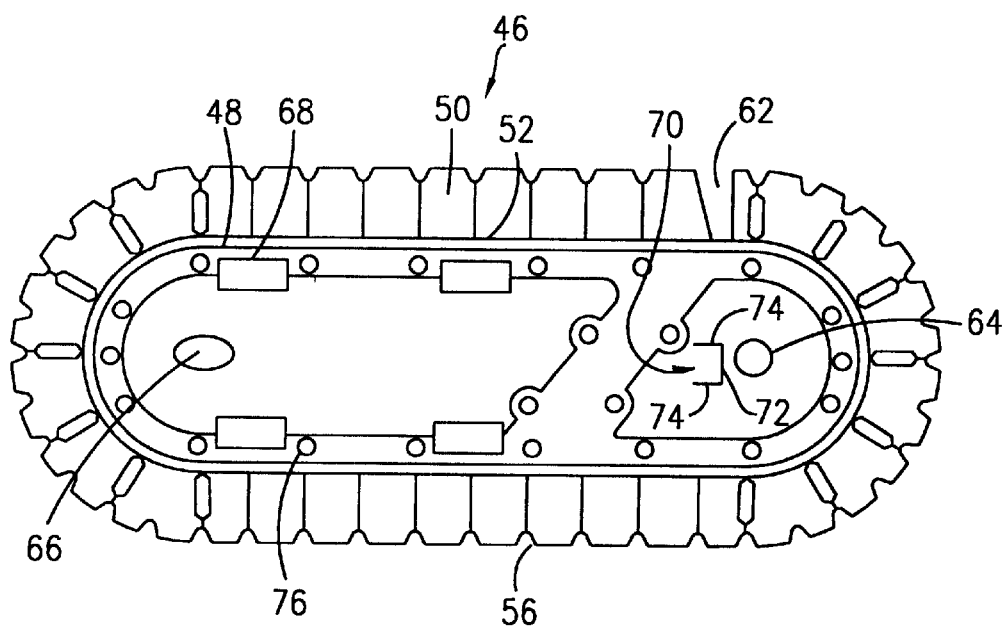
FIG. 5 is a top view of a suture channel cover adapted for use with the base members shown in FIGS. 1–4.

FIG. 5 shows a suture channel cover 46, which is sized and shaped to cover the suture channel 24 and to secure the suture 41 therein. The suture channel cover 46 has a general shape substantially matching that of the base member 12, more particularly, matching that of the suture channel 24 thereof.

Referring to FIG. 5, the suture channel cover 46 has an upwardly extending wall 48 and a plurality of cover door members 50, which are connected to the wall 48 and extend outwardly therefrom. The cover door members 50 are cantilevered with plastic hinges 52. It will be understood that cantilevered cover door members 50 are merely exemplary, and that other cover door members 50 may be employed. Each cover door member 50 is moveable and the outer periphery of the cover door members 50 features a plurality of notches 56 which align with the standoff members 26 (FIG. 1) of the base member 12.

The suture channel cover 46 has a passageway 62 positioned under the passageway 28 (FIG. 1) when the suture channel cover 46 is placed on the base member 12. A circular winding pin hole 64 and an oval pin locating hole 66 align with wining pins of a conventional, rotatable winding fixture (not shown). Cover cleat retention holes 68 align with the cover cleat retention holes 36 (FIG. 1) of the base member 12. An optional lifting tab 70 has a main slit 72 and two side slits 74 perpendicular to the main slit 72 so as to form a living hinge member.

The suture channel cover 46 also includes a plurality of rivets 76 sized and shaped to be connected to the rivet retention holes 30 (FIG. 1) of the base member 12. It will be understood that the suture channel cover 46 may employ other conventional fastening devices, such as locking pins, screws, etc., to connect the suture channel cover 46 with the base member 12. As shown in FIG. 5, the wall 48 is intermediate the cover door members 50 and the rivets 76.

Figure 6A:
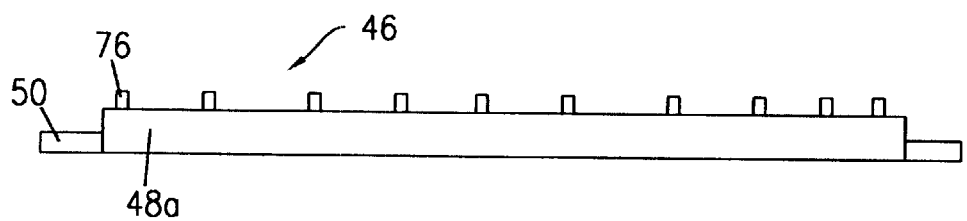
FIG. 6A is a side view of the suture channel cover of FIG. 5.
Figure 6B:
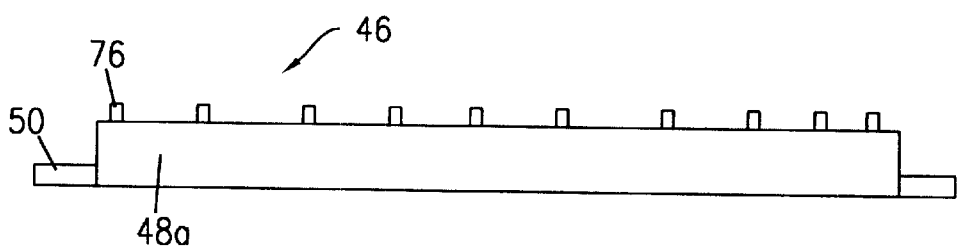
FIG. 6B is a side view of a suture channel cover similar to the one shown in FIG. 6A, but having a greater elevation to form a deeper suture channel.

The depth of the suture channel 24 is directly proportional to the height of the wall 48 of the suture channel cover 46. FIG. 6A illustrates a wall 48a for a standard size suture channel which may contain a single suture, while FIG. 6B illustrates a wall 48b for an extra depth suture channel which may contain multiple suture strands.

Figure 7:
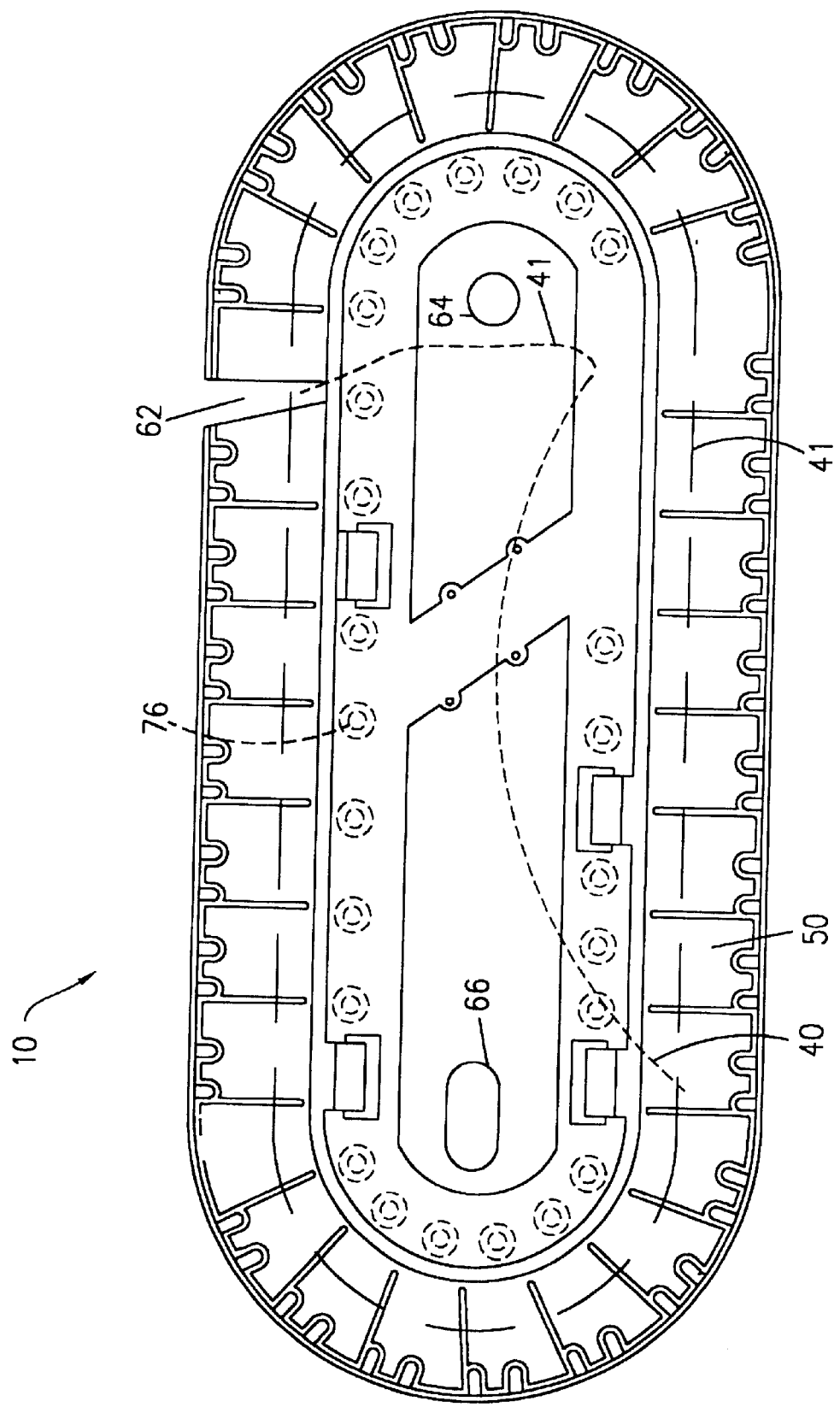
FIG. 7 is a bottom view of a tray package utilizing the base member of FIG. 1 in combination with the suture channel cover of FIG. 5.

FIG. 7 shows the tray package 10 with the suture channel cover 46 in place on the bottom surface 14 of the base member 12. In order to assemble the tray package 10, the base member 12 (FIG. 1) is aligned with the suture channel cover 46 (FIG. 5) such that the rivets 76 (FIG. 5) are in alignment with the rivet retention holes 30 (FIG. 1) of the base member 12.

Figure 9:
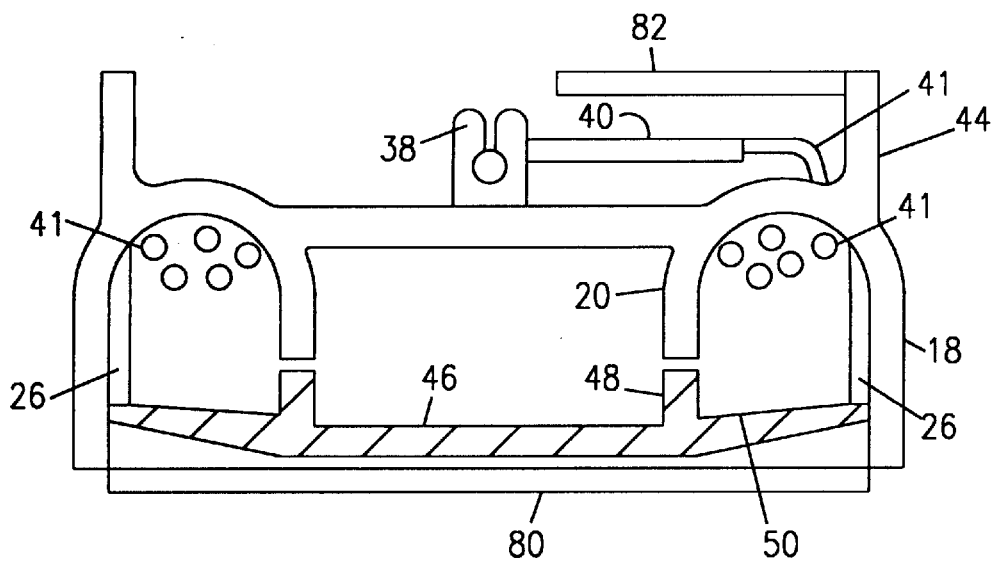
FIG. 9 is a simplified, diagrammatic cross-sectional view of the tray package of FIG. 8 after the tray package has been assembled, taken along line IX—IX and looking in the direction of the arrows.
Figure 10:
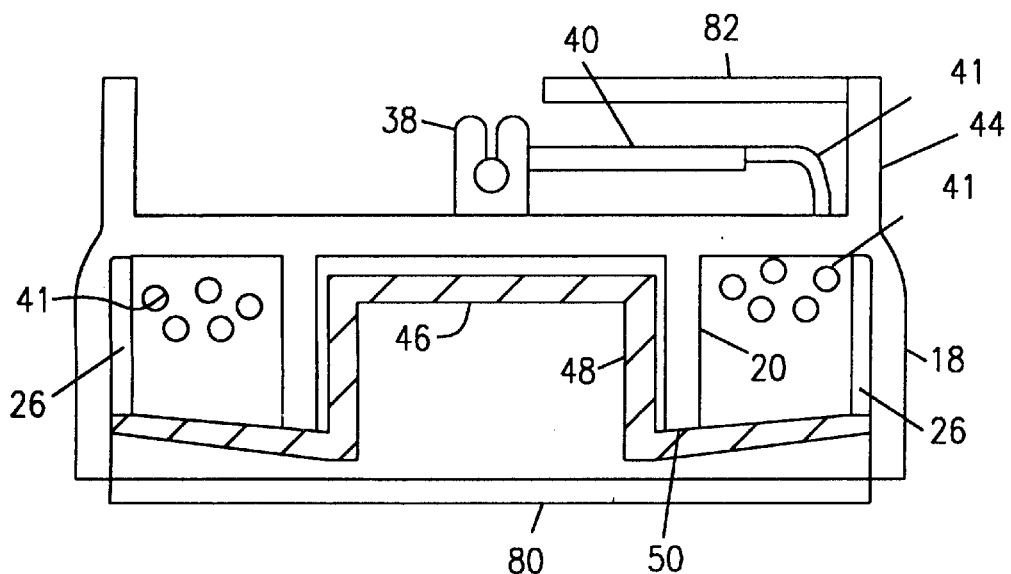
FIG. 10 is a cross-sectional view, similar to that of FIG. 9, showing a modified version of the tray package illustrated in FIG. 9.

Then, the suture channel cover 46 is mounted to the base member 12 such that the rivets 76 are inserted into and through the rivet retention holes 30. In this position, the standoff members 26 of the base member 12 will be positioned within the notches 56 of the suture channel cover 46. Also in this position, the inner wall 20 of the base member 12 is positioned directly above the wall 48 of the suture channel cover 46, as shown in FIG. 9. In an alternative embodiment, the inner wall 20 of the base member 12 is positioned adjacent the wall 48 of the suture channel cover 46 upon assembly of the base member 12 with the suture channel cover 46, as shown in FIG. 10. Thereafter, the ends of the rivets 76 are spread by using conventional techniques such as heating, ultrasonic treatments, etc., such that the suture channel cover 46 adheres to the base member 12 with the suture channel 24 covered by the cover door members 50.

The following discussion describes the insertion of a single armed suture 41 (FIG. 7) with the needle 40 into the tray package 10. Initially, the needle 40 is placed onto a separate fixture (not shown) which automatically places the needle 40 into the needle parks 38a–38e (FIG. 3) or the pins 42 (FIG. 4). The tray package 10 is then automatically flipped over and mounted into a conventional, rotatable winding fixture (not shown), such that the winding pins of the winding fixture are inserted through the circular winding pin hole 64 and the oval pin locating hole 66 as is known in the art. Also, the suture 41 is threaded through the passageway 28 such that the suture 41 traverses into the suture channel 24.

Then, the suture 41 is guided into the suture channel 24 by a conventional stylus that lifts the cover door members 50 as the tray package 10 is rotated in the winding fixture such that the suture 41 is completely wound in the suture channel 24 as the tray package 10 is rotated. The above-mentioned steps are repeated for additional sutures and needles.

Figure 8:
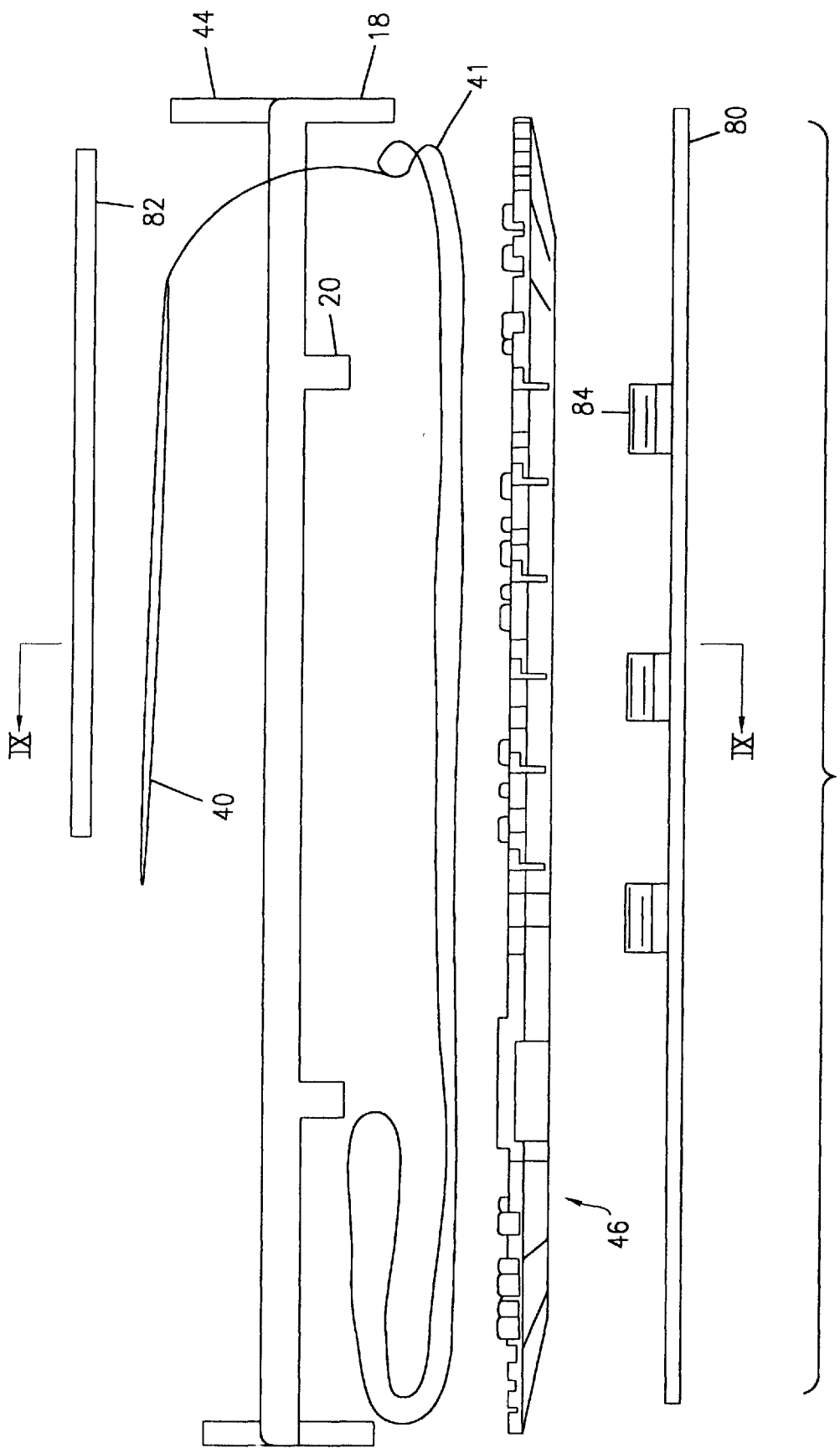
FIG. 8 is an exploded side view of the tray package of FIG. 7, taken from a top side of the tray package to a bottom side of the tray package.

The tray package 10 is shown with an optional bottom cover 80 (FIG. 8) mounted thereto, and another optional top cover 82 (FIG. 8) mounted thereto. The bottom and top covers 80, 82 are typically made from paper or cardboard. The bottom cover 80 completely covers the bottom surface 14 of the tray package 10 and has cleat members 84 (FIG. 8), which extend upwardly through the cover cleat retention holes 36, 68. Alternatively, the tray package 10 can use other attachment means, such as heat, adhesive, ultrasonic treatment, etc., to connect the bottom cover 80 to the bottom surface 14 rather than the cleat members 84 and the cover cleat retention holes 36, 68. With reference to FIG. 8, the top cover 82 covers only a portion of the bottom surface of the tray package 10 so that a needle grasper may grasp the needle 40.

The tray package 10 is sterilized after fabrication and loading by radiation, heat, ethylene oxide, or any other convenient and conventional method. After sterilization, the tray package 10 is hermetically sealed in an outer pouch or in an envelope to preserve sterility.

When employed during surgical procedures, a surgeon uses a conventional needle grasper to push down the optional lifting tab 70 from the top side (i.e., the side with the needle 40) through the bottom side (i.e., the side with the suture channel 24) so as to grasp and remove the needle 40 from the needle park, e.g. 38a. The needle 40 is then pulled away from the tray package 10 with the suture 41 pulling through the passageway 28 and being withdrawn from the suture channel 24.

As is evident from the description above, the tray package 10 is able to contain large and/or more needles compared to conventional tray packages of the same size and is readily adaptable to high-speed packaging processes, thereby overcoming the disadvantages of the prior art packages described above.

The foregoing description discloses only the preferred embodiments of the invention. Modifications of the above-disclosed apparatus that fall within the scope of the invention will be readily apparent to those of ordinary skill in the art. For example, the needle parks 38a–38e (FIG. 3) can be attached to the bottom surface 14 of the base member 12 and the suture channel 24 can be formed in the top surface 16 of the base member 12. Accordingly, while the present invention has been disclosed in connection with various exemplary embodiments thereof, it should be understood that other embodiments may fall within the spirit and scope of the invention, as defined by the following claims.

The invention claimed is:

1. A suture package comprising a base member having a top surface and a bottom surface opposite said top surface; first holding means, located on said top surface, for releaseably holding a needle, whereby a needle held by said first holding means is positioned on said top surface, said first holding means including a bridge extending from one side of said top surface to an opposite side of said top surface; and second holding means, depending from said bottom surface and extending in a direction opposite said first holding means, for holding a suture, whereby a suture held by said second holding means is positioned on said bottom surface.

2. The suture package of claim 1, wherein said first holding means includes a plurality of needle parks located on said bridge, each of said needle parks being sized and shaped to receive a needle held by said first holding means.

3. The suture package of claim 1, wherein said first holding means includes a plurality of pins mounted on said bridge.

4. The suture package of claim 2, wherein said second holding means includes a suture channel formed in said bottom surface of said base member.

5. The suture package of claim 4, wherein said suture channel includes an outer peripheral wall depending from said bottom surface: an inner peripheral wall depending from said bottom surface; and a portion of said bottom surface intermediate said inner peripheral wall and said outer peripheral wall.

6. The suture package of claim 5, further comprising a cover connected to said bottom surface and sized and shaped to cover said suture channel.

7. A suture package, comprising:

a base member having a top surface and a bottom surface opposite said top surface; first holding means, located on said top surface, for releaseably holding a needle; second holding means, located on said bottom surface, for holding a suture, whereby a needle held by said first holding means is positioned on said top surface and whereby a suture held by said second holding means is positioned on said bottom surface, said first holding means including a bridge extending from one side of said top surface to an opposite side of said top surface, said first holding means including a plurality of needle parks located on said bridge, each of said needle parks being sized and shaped to receive a needle held by said first holding means, said second holding means including a suture channel formed in said bottom surface of said base member, said suture channel including an outer peripheral wall depending from said bottom surface, an inner peripheral wall depending from said bottom surface, and a portion of said bottom surface intermediate said inner peripheral wall and said outer peripheral wall; and a cover connected to said bottom surface and sized and shaped to cover said suture channel, said cover including an intermediate wall and a plurality of cantilevered doors attached to said intermediate wall.

8. The suture package of claim 7, wherein said suture channel has a depth and said intermediate wall of said cover has a height; and wherein said depth of said suture channel is proportional to said height of said intermediate wall of said cover.

9. The suture package of claim 8, wherein said intermediate wall of said cover is positioned adjacent said inner peripheral wall of said bottom surface of said base member.

10. The suture package of claim 8, wherein said intermediate wall of said cover is aligned with said inner peripheral wall of said bottom surface of said base member.

11. The suture package of claim 7, wherein said base member has a passageway so as to allow a suture held by said second holding means to traverse between said bottom surface and said top surface of said base member.

12. The suture package of claim 11, wherein said top surface of said base member includes an outer wall sized and shaped to surround a needle held by said first holding means.

\* \* \* \* \*